(12) United States Patent
Schlun

(10) Patent No.: US 8,196,279 B2
(45) Date of Patent: Jun. 12, 2012

(54) STENT-GRAFT COVERING PROCESS

(75) Inventor: Martin Schlun, Herxheim Bei Landau/Pfalz (DE)

(73) Assignee: C. R. Bard, Inc., Murray Hill, NJ (US)

( * ) Notice: Subject to any disclaimer, the term of this patent is extended or adjusted under 35 U.S.C. 154(b) by 576 days.

(21) Appl. No.: 12/392,057

(22) Filed: Feb. 24, 2009

(65) Prior Publication Data
US 2009/0211076 A1 Aug. 27, 2009

Related U.S. Application Data

(60) Provisional application No. 61/031,818, filed on Feb. 27, 2008.

(51) Int. Cl.
*B23P 11/02* (2006.01)
(52) U.S. Cl. .......................................................... 29/505
(58) Field of Classification Search .................... 29/458, 29/505, 507, 428, 506, 460; 623/1.15, 1.44; 427/2.1, 2.24, 2.25
See application file for complete search history.

(56) References Cited

U.S. PATENT DOCUMENTS

| | | | |
|---|---|---|---|
| 612,897 A | 10/1898 | Ellis | |
| 3,060,517 A | 10/1962 | Fields | |
| 3,196,194 A | 7/1965 | Ely, Jr. et al. | |
| 3,207,601 A | 9/1965 | Barry | |
| 3,281,511 A | 10/1966 | Goldsmith | |
| 3,767,500 A | 10/1973 | Tally et al. | |
| 3,887,761 A | 6/1975 | Gore | |
| 3,992,725 A | 11/1976 | Homsy | |
| 4,061,517 A | 12/1977 | Dutton, III et al. | |
| 4,159,370 A | 6/1979 | Koizumi et al. | |
| 4,324,574 A | 4/1982 | Fagan | |
| RE31,341 E | 8/1983 | Koizumi et al. | |
| 4,416,028 A | 11/1983 | Eriksson et al. | |
| RE31,618 E | 7/1984 | Mano et al. | |
| 4,482,516 A | 11/1984 | Bowman et al. | |
| 4,503,569 A | 3/1985 | Dotter | |
| 4,512,338 A | 4/1985 | Balko et al. | |
| 4,580,568 A | 4/1986 | Gianturco | |
| 4,588,461 A | 5/1986 | Braun | |
| 4,596,837 A | 6/1986 | Yamamoto et al. | |
| 4,604,762 A | 8/1986 | Robinson | |
| 4,629,458 A | 12/1986 | Pinchuk | |
| 4,647,416 A | 3/1987 | Seiler, Jr. et al. | |
| 4,655,769 A | 4/1987 | Zachariades | |
| 4,665,906 A | 5/1987 | Jervis | |
| 4,714,748 A | 12/1987 | Hoashi et al. | |
| 4,731,073 A | 3/1988 | Robinson | |
| 4,733,665 A | 3/1988 | Palmaz | |
| 4,739,762 A | 4/1988 | Palmaz | |
| 4,747,849 A | 5/1988 | Galtier | |
| 4,760,102 A | 7/1988 | Moriyama et al. | |

(Continued)

FOREIGN PATENT DOCUMENTS

DE 3918736 12/1990
(Continued)

*Primary Examiner* — John C Hong
(74) *Attorney, Agent, or Firm* — Rutan & Tucker, LLP

(57) ABSTRACT

A method of making a stent-graft includes providing a self-expanding stent having a collapsed configuration with a first diameter and an expanded configuration with a second diameter greater than the first diameter, the stent including a polymeric coating on at least an inner surface, disposing a graft on a mandrel having a third diameter greater than the second diameter, and contacting an outer surface of the graft with the coated inner surface of the stent, the stent applying a compressive force to the graft.

15 Claims, 1 Drawing Sheet

U.S. PATENT DOCUMENTS

| | | |
|---|---|---|
| 4,767,418 A | 8/1988 | Deininger et al. |
| 4,776,337 A | 10/1988 | Palmaz |
| 4,816,339 A | 3/1989 | Tu et al. |
| 4,820,298 A | 4/1989 | Leveen et al. |
| 4,830,062 A | 5/1989 | Yamamoto et al. |
| 4,850,999 A | 7/1989 | Planck |
| 4,857,069 A | 8/1989 | Kira |
| 4,886,062 A | 12/1989 | Wiktor |
| 4,907,336 A | 3/1990 | Gianturco |
| 4,922,905 A | 5/1990 | Strecker et al. |
| 4,935,068 A | 6/1990 | Duerig |
| 4,954,126 A | 9/1990 | Wallsten et al. |
| 4,955,899 A | 9/1990 | Della Corna et al. |
| 4,957,669 A | 9/1990 | Primm |
| 4,969,458 A | 11/1990 | Wiktor |
| 4,969,896 A | 11/1990 | Shors |
| 5,019,090 A | 5/1991 | Pinchuk |
| 5,061,275 A | 10/1991 | Wallsten et al. |
| 5,061,276 A | 10/1991 | Tu et al. |
| 5,064,435 A | 11/1991 | Porter |
| 5,067,957 A | 11/1991 | Jervis |
| 5,071,609 A | 12/1991 | Tu et al. |
| 5,078,726 A | 1/1992 | Kreamer |
| 5,078,736 A | 1/1992 | Behl |
| 5,084,065 A | 1/1992 | Weldon et al. |
| 5,102,417 A | 4/1992 | Palmaz |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,124,523 A | 6/1992 | Oehlmann et al. |
| 5,133,732 A | 7/1992 | Wiktor |
| 5,135,503 A | 8/1992 | Abrams |
| 5,139,480 A | 8/1992 | Hickle et al. |
| 5,143,085 A | 9/1992 | Wilson |
| 5,152,782 A | 10/1992 | Kowligi et al. |
| 5,156,620 A | 10/1992 | Pigott |
| 5,158,548 A | 10/1992 | Lau et al. |
| 5,163,951 A | 11/1992 | Pinchuk et al. |
| 5,167,614 A | 12/1992 | Tessmann et al. |
| 5,171,805 A | 12/1992 | Tatemoto et al. |
| 5,192,307 A | 3/1993 | Wall |
| 5,195,984 A | 3/1993 | Schatz |
| 5,211,658 A | 5/1993 | Clouse |
| 5,219,355 A | 6/1993 | Parodi et al. |
| 5,219,361 A | 6/1993 | von Recum et al. |
| 5,231,989 A | 8/1993 | Middleman et al. |
| 5,234,456 A | 8/1993 | Silvestrini |
| 5,234,739 A | 8/1993 | Tanaru et al. |
| 5,236,446 A | 8/1993 | Dumon |
| 5,236,447 A | 8/1993 | Kubo et al. |
| 5,242,399 A | 9/1993 | Lau et al. |
| 5,258,027 A | 11/1993 | Berghaus et al. |
| 5,282,823 A | 2/1994 | Schwartz et al. |
| 5,282,824 A | 2/1994 | Gianturco |
| 5,282,847 A | 2/1994 | Trescony et al. |
| 5,282,848 A | 2/1994 | Schmitt |
| 5,282,849 A | 2/1994 | Kolff et al. |
| 5,282,860 A | 2/1994 | Matsuno et al. |
| 5,316,023 A | 5/1994 | Palmaz et al. |
| 5,330,500 A | 7/1994 | Song et al. |
| 5,334,201 A | 8/1994 | Cowan |
| 5,341,818 A | 8/1994 | Abrams et al. |
| 5,344,426 A | 9/1994 | Lau et al. |
| 5,349,964 A | 9/1994 | Imran et al. |
| 5,354,309 A | 10/1994 | Schnepp-Pesch et al. |
| 5,354,329 A | 10/1994 | Whalen |
| 5,360,443 A | 11/1994 | Barone et al. |
| 5,366,504 A | 11/1994 | Andersen et al. |
| 5,370,681 A | 12/1994 | Herweck et al. |
| 5,376,110 A | 12/1994 | Tu et al. |
| 5,382,261 A | 1/1995 | Palmaz |
| 5,383,106 A | 1/1995 | Yoshida et al. |
| 5,383,892 A | 1/1995 | Cardon et al. |
| 5,383,926 A | 1/1995 | Lock et al. |
| 5,383,928 A | 1/1995 | Scott et al. |
| 5,384,019 A | 1/1995 | Keating et al. |
| 5,385,580 A | 1/1995 | Schmitt |
| 5,387,235 A | 2/1995 | Chuter |
| 5,387,236 A | 2/1995 | Noishiki et al. |
| 5,389,106 A | 2/1995 | Tower |
| 5,395,390 A | 3/1995 | Simon et al. |
| 5,405,377 A | 4/1995 | Cragg |
| 5,405,378 A | 4/1995 | Strecker et al. |
| 5,411,476 A | 5/1995 | Abrams et al. |
| 5,421,955 A | 6/1995 | Lau et al. |
| 5,429,869 A | 7/1995 | McGregor et al. |
| 5,433,996 A | 7/1995 | Kranzler et al. |
| 5,437,083 A | 8/1995 | Williams et al. |
| 5,443,496 A | 8/1995 | Schwartz et al. |
| 5,449,373 A | 9/1995 | Pinchasik et al. |
| 5,452,726 A | 9/1995 | Burmeister et al. |
| 5,458,615 A | 10/1995 | Klemm et al. |
| 5,464,438 A | 11/1995 | Menaker |
| 5,464,440 A | 11/1995 | Johansson et al. |
| 5,464,449 A | 11/1995 | Ryan et al. |
| 5,474,563 A | 12/1995 | Myler et al. |
| 5,489,295 A | 2/1996 | Piplani et al. |
| 5,496,364 A | 3/1996 | Schmitt |
| 5,500,013 A | 3/1996 | Buscemi et al. |
| 5,507,767 A | 4/1996 | Maeda et al. |
| 5,507,768 A | 4/1996 | Lau et al. |
| 5,507,769 A | 4/1996 | Marin et al. |
| 5,507,771 A | 4/1996 | Gianturco |
| 5,514,115 A | 5/1996 | Frantzen et al. |
| 5,514,154 A | 5/1996 | Lau et al. |
| 5,522,881 A | 6/1996 | Lentz |
| 5,522,883 A | 6/1996 | Slater et al. |
| 5,523,092 A | 6/1996 | Hanson et al. |
| 5,527,353 A | 6/1996 | Schmitt |
| 5,527,355 A | 6/1996 | Ahn |
| 5,540,712 A | 7/1996 | Kleshinski et al. |
| 5,540,713 A | 7/1996 | Schnepp-Pesch et al. |
| 5,546,646 A | 8/1996 | Williams et al. |
| 5,549,635 A | 8/1996 | Solar |
| 5,549,663 A | 8/1996 | Cottone, Jr. |
| 5,554,181 A | 9/1996 | Das |
| 5,556,389 A | 9/1996 | Liprie |
| 5,556,414 A | 9/1996 | Turi |
| 5,556,426 A | 9/1996 | Popadiuk et al. |
| 5,562,725 A | 10/1996 | Schmitt et al. |
| 5,569,295 A | 10/1996 | Lam |
| 5,571,170 A | 11/1996 | Palmaz et al. |
| 5,571,171 A | 11/1996 | Barone et al. |
| 5,571,173 A | 11/1996 | Parodi et al. |
| 5,573,520 A | 11/1996 | Schwartz et al. |
| 5,591,197 A | 1/1997 | Orth et al. |
| 5,591,222 A | 1/1997 | Susawa et al. |
| 5,591,223 A | 1/1997 | Lock et al. |
| 5,591,224 A | 1/1997 | Schwartz et al. |
| 5,591,228 A | 1/1997 | Edoga |
| 5,591,229 A | 1/1997 | Parodi et al. |
| 5,593,417 A | 1/1997 | Rhodes |
| 5,597,378 A | 1/1997 | Jervis |
| 5,603,721 A | 2/1997 | Lau et al. |
| 5,607,445 A | 3/1997 | Summers |
| 5,607,478 A | 3/1997 | Lentz et al. |
| 5,609,624 A | 3/1997 | Kalis |
| 5,620,763 A | 4/1997 | House et al. |
| 5,628,786 A | 5/1997 | Banas et al. |
| 5,628,788 A | 5/1997 | Pinchuk |
| 5,630,806 A | 5/1997 | Inagaki et al. |
| 5,630,829 A | 5/1997 | Lauterjung |
| 5,630,840 A | 5/1997 | Mayer |
| 5,632,840 A | 5/1997 | Campbell |
| 5,639,278 A | 6/1997 | Dereume et al. |
| 5,645,559 A | 7/1997 | Hachtman et al. |
| 5,649,950 A | 7/1997 | Bourne et al. |
| 5,649,977 A | 7/1997 | Campbell |
| 5,653,727 A | 8/1997 | Wiktor |
| 5,653,747 A | 8/1997 | Dereume et al. |
| 5,665,117 A | 9/1997 | Rhodes |
| 5,667,523 A | 9/1997 | Bynon et al. |
| 5,674,241 A | 10/1997 | Bley et al. |
| 5,676,671 A | 10/1997 | Inoue et al. |
| 5,681,345 A | 10/1997 | Euteneuer |
| 5,683,448 A | 11/1997 | Cragg |

| Patent No. | Date | Inventor |
|---|---|---|
| 5,683,453 A | 11/1997 | Palmaz |
| 5,693,085 A | 12/1997 | Buirge et al. |
| 5,693,088 A | 12/1997 | Lazarus |
| 5,700,285 A | 12/1997 | Myers et al. |
| 5,700,286 A | 12/1997 | Tartaglia et al. |
| 5,713,949 A | 2/1998 | Jayaraman et al. |
| 5,716,393 A | 2/1998 | Lindenberg et al. |
| 5,718,159 A | 2/1998 | Thompson |
| 5,718,973 A | 2/1998 | Lewis et al. |
| 5,719,873 A | 2/1998 | Yamashita et al. |
| 5,723,003 A | 3/1998 | Winston et al. |
| 5,723,004 A | 3/1998 | Dereume et al. |
| 5,728,131 A | 3/1998 | Frantzen et al. |
| 5,728,158 A | 3/1998 | Lau et al. |
| 5,735,892 A | 4/1998 | Myers et al. |
| 5,735,893 A | 4/1998 | Lau et al. |
| 5,738,674 A | 4/1998 | Williams et al. |
| 5,749,880 A | 5/1998 | Banas et al. |
| 5,755,770 A | 5/1998 | Ravenscroft |
| 5,755,774 A | 5/1998 | Pinchuk |
| 5,755,781 A | 5/1998 | Jayaraman et al. |
| 5,766,238 A | 6/1998 | Lau et al. |
| 5,769,817 A | 6/1998 | Burgmeier |
| 5,769,884 A | 6/1998 | Solovay |
| 5,776,161 A | 7/1998 | Globerman et al. |
| 5,782,904 A | 7/1998 | White et al. |
| 5,788,626 A | 8/1998 | Thompson |
| 5,800,512 A | 9/1998 | Lentz et al. |
| 5,810,870 A | 9/1998 | Myers et al. |
| 5,824,037 A | 10/1998 | Fogarty et al. |
| 5,824,043 A | 10/1998 | Cottone, Jr. |
| 5,824,046 A | 10/1998 | Smith et al. |
| 5,824,054 A | 10/1998 | Khosravi et al. |
| 5,843,161 A | 12/1998 | Solovay |
| 5,843,166 A | 12/1998 | Lentz et al. |
| 5,849,037 A | 12/1998 | Frid et al. |
| 5,851,232 A | 12/1998 | Lois |
| 5,863,366 A | 1/1999 | Snow |
| 5,871,536 A | 2/1999 | Lazarus |
| 5,871,537 A | 2/1999 | Holman et al. |
| 5,873,906 A | 2/1999 | Lau et al. |
| 5,876,448 A | 3/1999 | Thompson et al. |
| 5,919,225 A | 7/1999 | Lau et al. |
| 5,925,061 A | 7/1999 | Ogi et al. |
| 5,928,279 A | 7/1999 | Shannon et al. |
| 5,961,545 A | 10/1999 | Lentz et al. |
| 6,001,125 A | 12/1999 | Golds et al. |
| 6,004,348 A | 12/1999 | Banas et al. |
| 6,010,530 A | 1/2000 | Goicoechea |
| 6,015,431 A | 1/2000 | Thornton et al. |
| 6,036,724 A | 3/2000 | Lentz et al. |
| 6,039,755 A | 3/2000 | Edwin et al. |
| 6,042,605 A | 3/2000 | Martin et al. |
| 6,048,484 A | 4/2000 | House et al. |
| 6,120,535 A | 9/2000 | McDonald et al. |
| 6,124,523 A | 9/2000 | Banas et al. |
| 6,139,573 A | 10/2000 | Sogard et al. |
| 6,149,681 A | 11/2000 | Houser et al. |
| 6,165,210 A | 12/2000 | Lau et al. |
| 6,214,039 B1 | 4/2001 | Banas et al. |
| 6,306,141 B1 | 10/2001 | Jervis |
| 6,309,343 B1 | 10/2001 | Lentz et al. |
| 6,309,413 B1 | 10/2001 | Dereume et al. |
| 6,312,454 B1 | 11/2001 | Stockel et al. |
| 6,364,903 B2 | 4/2002 | Tseng et al. |
| 6,364,904 B1 | 4/2002 | Smith |
| 6,375,787 B1 | 4/2002 | Lukic et al. |
| 6,379,379 B1 | 4/2002 | Wang |
| 6,383,214 B1 | 5/2002 | Banas et al. |
| 6,398,803 B1 | 6/2002 | Layne et al. |
| 6,451,052 B1 | 9/2002 | Burmeister et al. |
| 6,488,701 B1 | 12/2002 | Nolting et al. |
| 6,524,334 B1 | 2/2003 | Thompson |
| 6,547,814 B2 | 4/2003 | Edwin et al. |
| 6,579,314 B1 | 6/2003 | Lombardi et al. |
| 6,673,103 B1 | 1/2004 | Golds et al. |
| 6,673,105 B1 | 1/2004 | Chen |
| 6,733,524 B2 | 5/2004 | Tseng et al. |
| 6,740,115 B2 | 5/2004 | Lombardi et al. |
| 6,758,858 B2 | 7/2004 | McCrea et al. |
| 6,770,086 B1 | 8/2004 | Girton |
| 6,786,920 B2 | 9/2004 | Shannon et al. |
| 6,790,225 B1 | 9/2004 | Shannon et al. |
| 6,797,217 B2 | 9/2004 | McCrea et al. |
| 6,808,533 B1 | 10/2004 | Goodwin et al. |
| 7,060,150 B2 | 6/2006 | Banas et al. |
| 7,083,640 B2 | 8/2006 | Lombardi et al. |
| 7,462,190 B2 | 12/2008 | Lombardi |
| 7,468,071 B2 | 12/2008 | Edwin et al. |
| 2001/0010012 A1 | 7/2001 | Edwin et al. |
| 2001/0039446 A1 | 11/2001 | Edwin et al. |
| 2002/0040237 A1 | 4/2002 | Lentz et al. |
| 2003/0004559 A1 | 1/2003 | Lentz et al. |
| 2003/0006528 A1 | 1/2003 | Edwin et al. |
| 2003/0144725 A1 | 7/2003 | Lombardi |
| 2004/0024442 A1 | 2/2004 | Sowinski et al. |
| 2004/0162603 A1 | 8/2004 | Golds et al. |
| 2004/0162604 A1 | 8/2004 | Sowinski et al. |
| 2004/0181278 A1 | 9/2004 | Tseng et al. |
| 2004/0204757 A1 | 10/2004 | Lombardi et al. |
| 2004/0236400 A1 | 11/2004 | Edwin et al. |
| 2005/0055081 A1 | 3/2005 | Goodwin et al. |
| 2005/0060020 A1 | 3/2005 | Jenson |
| 2005/0096737 A1 | 5/2005 | Shannon et al. |
| 2005/0113909 A1 | 5/2005 | Shannon et al. |
| 2005/0131515 A1 | 6/2005 | Cully et al. |
| 2005/0131527 A1 | 6/2005 | Pathak |
| 2007/0207186 A1 | 9/2007 | Scanlon et al. |

FOREIGN PATENT DOCUMENTS

| | | |
|---|---|---|
| DE | 19524653 A1 | 6/1996 |
| EP | 461791 | 12/1991 |
| EP | 551179 | 7/1993 |
| EP | 603959 | 6/1994 |
| EP | 0603959 A1 | 6/1994 |
| EP | 734698 | 10/1996 |
| EP | 0734698 | 10/1996 |
| EP | 749729 | 12/1996 |
| EP | 792627 A2 | 9/1997 |
| EP | 893108 A2 | 1/1999 |
| FR | 2671482 A1 | 7/1992 |
| GB | 1505591 | 3/1978 |
| GB | 2281865 | 3/1995 |
| WO | WO-9412136 | 6/1994 |
| WO | WO-9413224 A1 | 6/1994 |
| WO | WO-9424961 A1 | 11/1994 |
| WO | WO-9505132 | 2/1995 |
| WO | WO-9600103 A1 | 1/1996 |
| WO | WO-9628115 | 9/1996 |
| WO | WO-9707751 A1 | 3/1997 |
| WO | WO-9721401 A1 | 6/1997 |
| WO | WO-9721403 A1 | 6/1997 |
| WO | WO-9800090 | 1/1998 |
| WO | WO-9826731 A2 | 6/1998 |
| WO | WO-9831305 | 7/1998 |
| WO | WO-9831306 | 7/1998 |
| WO | WO-9838947 A1 | 9/1998 |
| WO | WO-0045742 | 8/2000 |

STENT-GRAFT COVERING PROCESS

PRIORITY

This application claims the benefit of U.S. Provisional Patent Application No. 61/031,818, filed Feb. 27, 2008, which is incorporated by reference in its entirety into this application.

BACKGROUND

Intraluminal prostheses used to maintain, open, or dilate blood vessels are commonly known as stents. Stent constructions generally include lattice type cylindrical frames that define a plurality of openings. Stents may have self-expanding and/or balloon expandable properties. Stents can be made of various metals and polymers and can include a combination of self-expanding and balloon expandable properties.

Synthetic vascular grafts are routinely used to restore the blood flow in patients suffering from vascular diseases. For example, prosthetic grafts made from expanded polytetrafluoroethylene (ePTFE) are commonly used and have shown favorable patency rates, meaning that depending on a given time period, the graft maintains an open lumen for the flow of blood therethrough. Grafts formed of ePTFE include a microstructure characterized by spaced apart nodes connected by fibrils, the distance between the nodes defined as internodal distance (IND), and are generally extruded either as a tube or as a sheet or film that is fashioned into a tube.

It is known in the art to use stents in combination with vascular grafts or covering layers to form stent-grafts. A vascular graft or covering layer, such as an ePTFE tube, is positioned adjacent an inner and/or outer surface of the stent and adhered thereto. For instance, U.S. Pat. No. 6,004,348 to Banas et al., which is incorporated by reference in its entirety into this application, describes an encapsulated stent formed by providing a first ePTFE graft about a mandrel, concentrically positioning a stent about the first ePTFE graft, and concentrically positioning a second ePTFE graft about the stent. Circumferential pressure is then applied to the assembly by helically wrapping ePTFE tape under tension over the outer surface of the second ePTFE graft. Thereafter, the assembly is heated to bond the first ePTFE graft to the second ePTFE graft through the openings of the stent. Following the sintering process, the ePTFE tape is unwrapped from the assembly.

U.S. Pat. No. 6,214,039 to Banas et al. describes a method of forming a stent-graft with a single graft or covering layer disposed on the abluminal surface of the stent, including sliding an ePTFE graft over a tapered mandrel with an increasing diameter to dilate the ePTFE graft and then sliding the dilated graft onto an unexpanded stent such that the graft is retained about an outer surface of the stent by the inherent recoil properties of the graft. Methods of forming a stent-graft with a single graft or covering layer on the luminal surface of the stent generally involves the use of adhesives or coatings positioned on the stent and/or surface of the graft. For example, an ePTFE graft is placed on a mandrel and a stent with a polymeric coating is positioned over the graft. As with the encapsulation procedure described above, tape is then helically wrapped about the outer surface of the stent under tension and the stent-graft is heated to achieve bonding of the ePTFE graft to the coated stent. However, differently from the encapsulation procedure, removal of the tape from the stent-graft is often difficult due to the tendency of the stent coating to melt and bond to the tape, such that the removal process may result in tearing of the graft and/or deposit of tape fragments on the stent-graft (requiring manual removal).

It is advantageous to have a graft or covering layer on the luminal surface of the stent-graft in order to provide a smooth surface for the flow of blood through the stent-graft. Moreover, a stent-graft with a single luminal graft or covering layer may provide advantages over a stent-graft with two or more graft layers, such as providing a lower profile for insertion and increasing flexibility. Thus, a method of applying pressure to the stent-graft with a single luminal graft or covering layer is desirable.

References related to stent-grafts include: U.S. Pat. Nos. 6,004,348; 6,214,039; 6,364,903; 6,488,701; and U.S. Patent Application Publication No. 2005/0096737, each of which is incorporated by reference in its entirety into this application.

Applicants have recognized that it would be desirable to provide a method for forming a stent-graft with a single graft layer on the luminal surface of the stent, embodiments of which are described herein.

SUMMARY

Accordingly, described herein are methods for forming a stent-graft. In one embodiment, a method of making a stent-graft includes providing a self-expanding stent having a collapsed configuration with a first diameter and an expanded configuration with a second diameter greater than the first diameter, the stent including a polymeric coating on at least an inner surface, disposing a graft on a mandrel having a third diameter greater than the second diameter, and contacting an outer surface of the graft with the coated inner surface of the stent, the stent applying a compressive force to the graft.

In another embodiment, a method of making a stent-graft, includes providing a self-expanding stent having a collapsed configuration with a first diameter and an expanded configuration with a second diameter greater than the first diameter, the stent including a polymeric material on at least a portion of an inner surface, disposing an ePTFE graft on a mandrel having a third diameter about 1 mm greater than the second diameter, placing the stent onto the graft by expanding the stent to a fourth diameter greater than the third diameter, positioning the stent over the graft and releasing the stent, and heating the stent-graft.

In yet another embodiment, a method of making a stent-graft includes providing a self-expanding stent having a collapsed configuration with a first diameter and an expanded configuration with a second diameter greater than the first diameter, the stent including a polymeric coating on at least an inner surface, disposing an ePTFE graft on a mandrel having a third diameter greater than the second diameter, expanding the stent to a fourth diameter greater than the third diameter, positioning the stent over the graft and releasing the stent, the coated inner surface of the stent contacting an outer surface of the ePTFE graft, wrapping ePTFE tape about an outer surface of the stent under tension, and removing the ePTFE tape prior to subjecting the stent-graft to a heating step.

These and other embodiments, features and advantages will become more apparent to those skilled in the art when taken with reference to the following more detailed description of the invention in conjunction with the accompanying drawings that are first briefly described.

DETAILED DESCRIPTION

Figure 1A:
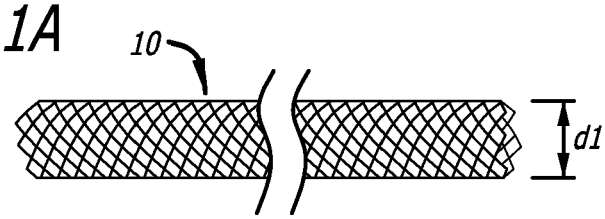
FIG. 1A is a partial side view of a stent in a collapsed configuration.

The following description should be read with reference to the drawings, in which like elements in different drawings are identically numbered. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

Described herein is a process to create a stent-graft assembly, including a stent with an single graft layer, without using an outer wrapping of tape during a heating step. A stent-graft employing a single graft layer (as opposed to multiple layers) increases flexibility and reduces the overall delivery system profile. However, creating a single graft layer stent-graft has proved more difficult than a dual graft layer stent-graft, in which an inner graft layer is bonded to an outer graft layer with the stent positioned therebetween. This is due to the fact that the dual graft layer stent-graft utilizes graft-to-graft bonding, whereas the single graft layer stent-graft must bond to the stent surface. Thus, a coating or adhesive is generally applied to the stent surface in order to achieve sufficient bonding between the stent and the graft layer in a single graft layer stent-graft. However, whereas in a dual layer stent-graft an outer tape wrap can be applied to the outer graft layer to aid in bonding of the graft layers by applying external pressure, such an aid can prove problematic in a single graft layer stent-graft, at least where the single layer is positioned against the luminal surface of the stent. This is due to the outer tape wrap adhering to the coating (or a film layer, such as Kapton film, positioned over the outer surface of the stent prior to wrapping with tape) during a heating step, making removal thereof difficult and potentially damaging to the stent-graft. Accordingly, described herein is a process for creating a single graft layer stent-graft that overcomes the problems inherent in providing external pressure via a tape wrap to aid in bonding during a heating process and increases the bond strength between a single inner graft layer and a stent to reduce potential complications associated with delamination or separation of the graft layer from the stent.

Figure 1B:
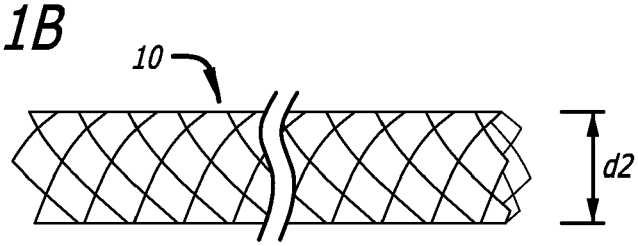
FIG. 1B is a partial side view of a stent in an expanded configuration.

A method of creating a single layer stent-graft is shown in FIGS. 1A-1D. FIG. 1A illustrates a first step in which an expandable stent is provided. Stent 10 has a first diameter d1, while in a collapsed configuration to assist in the implant delivery procedure. In an expanded configuration, the stent 10 has a second diameter d2, as shown in FIG. 1B. The diameter d2 of the expanded configuration is greater that the diameter d1 in the collapsed configuration. When implanted, the stent deploys to an expanded configuration in order to open a body lumen and permit blood flow therethrough. Therefore, the expanded diameter d2 is sufficient to hold open a patient's body lumen. Generally, the expanded diameter d2 is about 4 mm to about 8 mm. The process described herein may be employed with any stent design, including self-expanding stents or balloon expandable stents, although the preferred embodiment is self-expanding stents. The stent may be designed to collapse or expand radially in a uniform or non-uniform fashion to assist during delivery. The stent is generally sufficiently rigid to remain open when inserted into a body lumen. The stent may be formed of a shape memory material, including, for example, shape memory metals, shape memory alloys, super elastic shape memory metal alloys, linear elastic shape memory alloys, metal alloys, shape memory polymers, polymers, bio-resorbable material, and combinations thereof. One preferred shape memory material is Nitinol. The stent may alternatively be formed of metal, such as, for example, stainless steel, platinum, and Elgiloy, or certain polymers.

In one embodiment, the stent is coated with a polymeric bonding layer in order to secure a stent surface to a graft layer. The bonding layer may be applied by powder coating, spray coating, dipping in a liquid, or other methods known to one skilled in the art. The polymer can be PTFE, PET, fluorinated ethylene propylene (FEP), etc., or any other fluoropolymer. The polymeric coating may, additionally, be a combination of coatings, such as, for example, a first coat of PTFE and then a top coat of FEP.

Figure 1C:
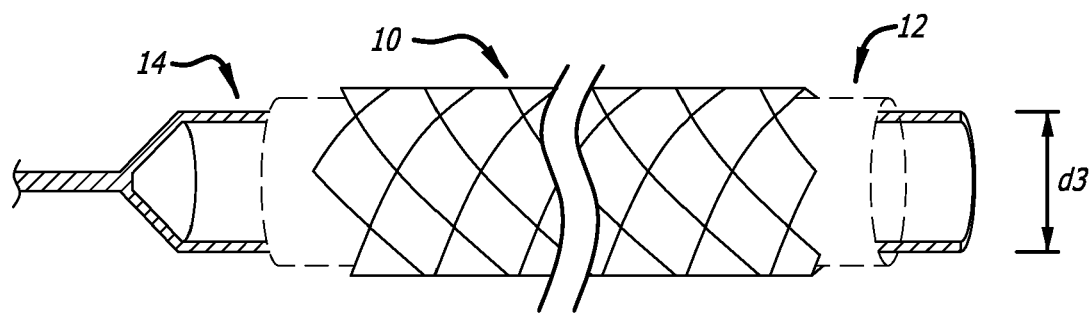
FIG. 1C is a partial side view of a graft and stent positioned on a mandrel.

As shown in FIG. 1C, a graft layer 12 is positioned on a mandrel 14 and the stent 10 is positioned over the graft layer 12. The graft layer 12 is generally a tubular member as indicated by the dotted line. The graft layer 12 may extend past the end of the stent during assembly, as shown in FIG. 1C, or may be coextensive therewith. The relative lengths of the stent and graft are illustrated for clarity only. Preferably, the graft layer terminates at about the ends of the stent or proximal of the stent ends. The graft material may include, for example, expanded polytetrafluoroethylene (ePTFE), polymer, polyurethane, fluoropolymers, such as perfouorelastomers and the like, silicones, urethanes, ultra high molecular weight polyethylene, aramid fibers, and combinations thereof. The graft may be made by any method. A tape may be wound helically to form a tube, or a sheet may be rolled into a tube. A graft formed in this way may be wrapped directly onto the mandrel, before the stent is disposed about the mandrel. Preferably, the graft is an extruded ePTFE tube. A graft formed in this way may be slid directly onto the mandrel 14. Alternatively, the graft may be folded and positioned within the stent. The graft and stent are then properly positioned, and the mandrel is inserted through the graft lumen. The wall thickness of the graft may be in the range of about 40 microns to about 200 microns, but generally less than about 100 microns. Preferably the wall thickness is between about 40 microns and about 100 microns.

According to one embodiment, a method of making a stent-graft includes providing an expandable stent, which is coated at least on an inner surface thereof, disposing a graft on a mandrel, and contacting the outer surface of the graft with the coated inner surface of the stent. As shown in FIG. 1C, a mandrel 14 has a third diameter d3 that is greater than the stent expanded diameter d2. The mandrel diameter d3 in one embodiment is less than about 2 mm greater than the expanded stent diameter d2. Preferably, the mandrel diameter d3 is about 0.1 mm to about 0.3 mm greater than the expanded stent diameter d2. However, the mandrel diameter should not exceed the stent diameter at which plastic deformation occurs. Because the mandrel diameter exceeds the stent expanded diameter, the stent supplies a compressive force to the graft 12 when the stent 10 is positioned over the graft, the compressive or external force aiding in bonding of the graft 12 to the stent 10.

Figure 1D:
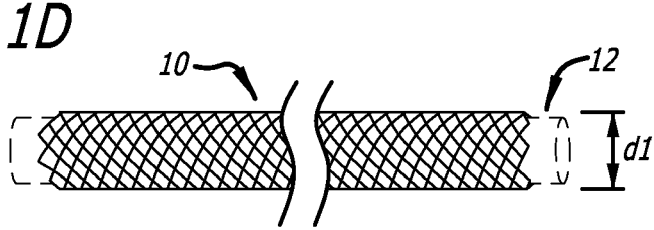
FIG. 1D is a partial side view of the bonded stent-graft after removal from a mandrel.

The graft may be disposed on the mandrel by sliding a generally tubular graft onto the mandrel. Alternatively, an ePTFE film may be wrapped around the mandrel. An ePTFE tape may be helically wrapped around the mandrel to form a generally cylindrical tube over the mandrel, or a ePTFE sheet may be wrapped around the mandrel to form the generally cylindrical tube. The stent is then placed over the mandrel and the graft. To place the stent over the mandrel, the stent may be expanded to a fourth diameter, greater than the mandrel diameter d3 and then released after it is properly positioned over the graft layer. A tool may be used to facilitate this step. Alternatively, the stent can be placed over the mandrel by first folding the graft and properly positioning it within the stent, followed by inserting the mandrel through the graft lumen. The stent-graft, after being positioned on the mandrel, may be wrapped to create a greater compressive force between the stent and graft layer. An ePTFE tape may be wrapped around the outer surface of the stent-graft assembly. The stent-graft may be wrapped with tape in helical windings. A second layer of tape may be wrapped in the opposite direction of the first tape layer to create an additional compressive uniform force. The tape is applied under tension, during the wrapping step. However, in embodiments where the stent-graft is heated, the tape is removed before the heating step. FIG. 1D shows the stent-graft removed from the mandrel and collapsed to a collapsed diameter, e.g., about the diameter d1, for implantation into a patient.

In one embodiment, the stent-graft assembly on the mandrel is inserted into an oven or other heating apparatus to strengthen the bond between the polymeric stent coating and the graft layer. Additional bond strength between the stent and the graft material is achieved by heating the assembly above the melting temperature of the polymeric coating. The melted polymer between the stent and the graft penetrates into the graft material, which is porous. The graft and stent may be heated to a temperature in the range of about 320 degrees C. to about 360 degrees Celsius, preferably heated to about 340 degrees C. for about 10 to 11 minutes. The stent-graft may be pre-wrapped with tape under tension to aid in bonding of the graft to the stent prior to heating and remain wrapped about the stent-graft for several minutes. Preferably, the stent-graft is pre-wrapped for a period in the range of about 5 minutes to about 10 minutes before removing the tape; however, in some embodiments, the tape may remain on the stent-graft assembly for a longer period.

By way of non-limiting illustration, specific embodiments of the method described herein are provided. In one embodiment, a self-expanding stent, having a 6 mm expanded diameter and a coating including a primer coat of PTFE and a top coat of FEP, was provided. A 7 mm ePTFE tubular graft layer was disposed over a 7 mm mandrel and the stent was expanded greater than about 7 mm, positioned over the graft layer, and released. The assembly was then heated to about 340 degrees C. for approximately 10.5 minutes. Following the heating step, the bond strength of the assembly was tested by performing a bond peel test. The procedure includes placing an end portion of the stent and an end portion of the graft in a tensile testing apparatus. For example, the end portion of the graft is inverted through the lumen of the stent-graft and placed in a clamp of the apparatus opposite the clamp of the apparatus holding the end portion of the stent. These end portions are then pulled apart by the tensile testing apparatus and a bond strength (gF/mm) is recorded at intervals along the stent-graft. An average of the bond strengths is then calculated. The average bond peel strength in the above-described embodiment was about 9.5 gF/mm. Generally, the bond strength for the stent-graft was in the range of about 2 gF/mm to about 13 gF/mm.

In another embodiment, the same materials and process as the above-described embodiment were employed, but the stent-graft assembly was tape-wrapped prior to heating. The stent-graft assembly was helically wrapped with ePTFE tape in two layers: a first layer in a first direction, and a second layer over the first layer in a second direction opposite the first direction. The tape was then removed after approximately 5 to 10 minutes. The stent-graft assembly, without the tape, was then heated to approximately 340 degrees Celsius for about 10.5 minutes. A bond peel test was performed and the average bond strength was about 12.3 gF/mm. Generally, the bond strength was in the range of about 4 gF/mm to about 14 gF/mm.

This invention has been described and specific examples have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method of making a stent-graft, comprising:
   providing a self-expanding stent having a collapsed configuration with a first diameter and an expanded configuration with a second diameter greater than the first diameter, the stent including a polymeric coating on at least an inner surface;
   disposing a graft on a mandrel having a third diameter greater than the second diameter; and
   contacting an outer surface of the graft with the coated inner surface of the stent, the stent applying a compressive force to the graft.

2. The method according to claim 1, wherein the contacting step comprises expanding the stent to a fourth diameter greater than the third diameter, positioning the stent over the graft and releasing the stent.

3. The method according to claim 1, further comprising the step of heating the stent-graft.

4. The method according to claim 3, wherein the heating step includes processing at a temperature of about 340 degrees C. for a time period in the range of about 10 minutes to about 11 minutes.

5. The method according to claim 1, wherein the disposing step includes sliding a generally tubular ePTFE graft onto the mandrel.

6. The method according to claim 1, wherein the disposing step includes wrapping an ePTFE film about the mandrel, the ePTFE film having a thickness in the range of about 40 microns to about 100 microns.

7. The method according to claim 1, wherein the providing step includes providing a stent comprised of shape memory metal.

8. The method according to claim 1, wherein the third diameter is in the range of about 0.1 mm to about 1 mm greater than the second diameter.

9. The method according to claim 8, wherein the second diameter is in the range of about 4 mm to about 14 mm.

10. The method according to claim 1, wherein the polymeric coating comprises PTFE.

11. The method according to claim 1, wherein the bond strength of the stent-graft is in the range of about 2 gf/mm to about 13 gf/mm.

12. The method according to claim 1, further comprising wrapping ePTFE tape about an outer surface of the stent under tension and heating the stent-graft, wherein the tape is removed from the stent before the heating step.

13. The method according to claim 12, wherein the ePTFE tape is removed from the stent after a period in the range of about 5 minutes to about 10 minutes.

14. The method according to claim 12, wherein the wrapping step comprises helically wrapping a first and second layer of tape about the outer surface of the stent.

15. The method according to claim 12, wherein the bond strength of the stent-graft is in the range of about 4 gf/mm to about 14 gf/mm.

* * * * *